United States Patent
Bigner et al.

(10) Patent No.: US 11,506,666 B2
(45) Date of Patent: Nov. 22, 2022

(54) DETECTION OF CD-155, THE POLIOVIRUS RECEPTOR

(71) Applicant: Duke University, Durham, NC (US)

(72) Inventors: Darell D. Bigner, Mebane, NC (US); Vidyalakshmi Chandramohan, Durham, NC (US); Matthias Gromeier, Durham, NC (US)

(73) Assignee: Duke University, Durham, NC (US)

( * ) Notice: Subject to any disclaimer, the term of this patent is extended or adjusted under 35 U.S.C. 154(b) by 670 days.

(21) Appl. No.: 16/340,026

(22) PCT Filed: Oct. 2, 2017

(86) PCT No.: PCT/US2017/054733
§ 371 (c)(1),
(2) Date: Apr. 5, 2019

(87) PCT Pub. No.: WO2018/067446
PCT Pub. Date: Apr. 12, 2018

(65) Prior Publication Data
US 2021/0311063 A1    Oct. 7, 2021

Related U.S. Application Data

(60) Provisional application No. 62/404,945, filed on Oct. 6, 2016.

(51) Int. Cl.
*G01N 33/574* (2006.01)
*C07K 16/28* (2006.01)
*G01N 33/58* (2006.01)
*G01N 33/60* (2006.01)

(52) U.S. Cl.
CPC .......... *G01N 33/57484* (2013.01); *C07K 16/2896* (2013.01); *G01N 33/582* (2013.01); *G01N 33/60* (2013.01); *C07K 2317/20* (2013.01); *C07K 2317/34* (2013.01); *G01N 2333/70596* (2013.01); *G01N 2333/908* (2013.01)

(58) Field of Classification Search
CPC combination set(s) only.
See application file for complete search history.

(56) References Cited

U.S. PATENT DOCUMENTS

| | | |
|---|---|---|
| 6,264,940 B1 | 7/2001 | Gromeier |
| 6,518,033 B1 | 2/2003 | Gromeier |
| 8,066,983 B2 | 11/2011 | Wimmer |
| 2005/0261170 A1 | 11/2005 | Hansen |
| 2017/0216382 A1 | 8/2017 | Gromeier |
| 2018/0296614 A1 | 10/2018 | Bigner |
| 2020/0046847 A1 | 2/2020 | Bigner |

FOREIGN PATENT DOCUMENTS

| | | |
|---|---|---|
| WO | 2017066557 A1 | 4/2017 |
| WO | 2017165266 A1 | 9/2017 |
| WO | 2018067446 A1 | 4/2018 |
| WO | 2018075357 A1 | 4/2018 |
| WO | 2019195302 A1 | 10/2019 |

OTHER PUBLICATIONS

Koike, S. et al. (1991) Proc. Natl. Acad. Sci. USA 88:4104. (Year: 1991).*
Belnap DM, et al. Three-dimensional structure of poliovirus receptor bound to poliovirus. Proc Natl Acad Sci U S A. 2000;97(1):73-78.
Bernhardt G, et al. The poliovirus receptor: identification of domains and amino acid residues critical for virus binding. Virology. 1994;203(2):344-356.
Bottino C, et al. Identification of PVR (CD155) and Nectin-2 (CD112) as cell surface ligands for the human DNAM-1 (CD226) activating molecule. J Exp Med. 2003;198(4):557-567.
Brown MC, et al. Oncolytic polio virotherapy of cancer. Cancer. 2014;120(21):3277-3286.
Brown MC, et al. "Cancer immunotherapy with recombinant poliovirus induces IFN-dominant activation of dendritic cells and tumor antigen-specific CTLs." Science translational medicine 9.408 (2017): eaan4220.
Brown MC, et al. Induction of viral, 7-methyl-guanosine cap-independent translation and oncolysis by mitogen-activated protein kinase-interacting kinase-mediated effects on the serine/arginine-rich protein kinase. J Virol. 2014;88(22):13135-13148.
Carlsten M, et al. Primary human tumor cells expressing CD155 impair tumor targeting by down-regulating DNAM-1 on NK cells. J Immunol. 2009;183(8):4921-4930.
Casado JG, et al. Expression of adhesion molecules and ligands for activating and costimulatory receptors involved in cell-mediated cytotoxicity in a large panel of human melanoma cell lines. Cancer Immunol Immunother. 2009;58(9):1517-1526.
Castriconi R, et al. NK cells recognize and kill human glioblastoma cells with stem cell-like properties. J Immunol. 2009;182(6):3530-3539.
Erickson BM, et al. Tightly regulated induction of the adhesion molecule necl-5/CD155 during rat liver regeneration and acute liver injury. Hepatology. 2006;43(2):325-334.
Freistadt MS, et al. Poliovirus receptor on human blood cells: a possible extraneural site of poliovirus replication. Virology. 1993;195(2):798-803.

(Continued)

*Primary Examiner* — Kimberly Ballard
*Assistant Examiner* — Stacey N MacFarlane
(74) *Attorney, Agent, or Firm* — Quarles & Brady LLP (57) ABSTRACT

A reliable assay to specifically detect CD155 in tissue sections has widespread use because CD155 is expressed widely among tumor types. Additionally, detected expression of CD 155 in glioblastoma cells is at levels commensurate with susceptibility to PVSRIPO (a poliovirus construct) infection and killing. An anti-CD155 antibody can achieve mono-specific detection of CD155 in immunoblots of tumor homogenates and immunohistochemistry of tumor formalin fixed, paraffin embedded sections. The assay can be used to determine appropriate use of PVSRIPO in oncolytic immunotherapy against cancers.

17 Claims, 8 Drawing Sheets
Specification includes a Sequence Listing.

(56) References Cited

OTHER PUBLICATIONS

Freistadt MS, et al. Heterogeneous expression of poliovirus receptor-related proteins in human cells and tissues. Mol Cell Biol. 1990;10(11):5700-5706.
Greenberg NM, et al. Prostate cancer in a transgenic mouse. Proc Natl Acad Sci U S A. 1995;92(8):3439-3443.
Gromeier M, et al. Intergeneric poliovirus recombinants for the treatment of malignant glioma. Proc Natl Acad Sci U S A. 2000;97(12):6803-6808.
He Y, et al. Interaction of the poliovirus receptor with poliovirus. Proc Natl Acad Sci U S A. 2000;97(1):79-84.
He Y, et al. Complexes of poliovirus serotypes with their common cellular receptor, CD155. J Virol. 2003;77(8):4827-4835.
International Searching Authority, International Search Report and Written Opinion for application PCT/US2017/054733, dated Oct. 2, 2017.
Iwasaki A, et al. Immunofluorescence analysis of poliovirus receptor expression in Peyer's patches of humans, primates, and CD155 transgenic mice: implications for poliovirus infection. J Infect Dis. 2002;186(5):585-592.
Koike S, et al. The poliovirus receptor protein is produced both as membrane-bound and secreted forms. EMBO J. 1990;9(10):3217-3224.
Martinet L, et al. Balancing natural killer cell activation through paired receptors. Nat Rev Immunol. 2015;15(4):243-254.
Matusali G, et al. The human immunodeficiency virus type 1 Nef and Vpu proteins downregulate the natural killer cell-activating ligand PVR. J Virol. 2012;86(8):4496-4504.
Mendelsohn CL, et al. Cellular receptor for poliovirus: molecular cloning, nucleotide sequence, and expression of a new member of the immunoglobulin superfamily. Cell. 1989;56(5):855-865.
Merrill, M. K., et al. "Poliovirus receptor CD155-targeted oncolysis of glioma." Neuro-oncology 6.3 (2004): 208-217.
Nobis, P., et al. "Production of a monoclonal antibody against an epitope on HeLa cells that is the functional poliovirus binding site." Journal of general virology 66.12 (1985): 2563-2569.
Reymond N, et al. DNAM-1 and PVR regulate monocyte migration through endothelial junctions. J Exp Med. 2004;199(10):1331-1341.
Sloan, K. E., et al. "CD155/PVR plays a key role in cell motility during tumor cell invasion and migration." BMC cancer 4.1 (2004): 73.
Solecki D, et al. The promoters for human and monkey poliovirus receptors. Requirements for basic and cell type-specific activity. J Biol Chem. 1997;272(9):5579-5586.
Wimmer E, et al. Poliovirus receptors. In "Cellular Receptors for Animal Viruses" (E. Wimmer, Ed.). Cold Spring Harbor Laboratory Press, Plainview, NY. 1993:pp. 101-128.

\* cited by examiner

| # | case no. | 3+ | 2+ | 1+ | +/- | - | endothelial cell staining 3+ | tumor status |
|---|---|---|---|---|---|---|---|---|
| 1 | 04-0474* | 100 | | | | | 100 | R |
| 2 | 13-0218* | 100 | | | | | 100 | ND |
| 3 | 09-0164* | 95 | | | | | 100 | R |
| 4 | 09-0043* | 90 | | | | | 100 | ND |
| 5 | 15-0259 | 95 | 5 | | | | 100 | ND |
| 6 | 10-0189 | 70 | 30 | | | | 100 | R |
| 7 | 13-0268 | 60 | 40 | | | | 100 | ND |
| 8 | 13-0056 | 50 | 50 | | | | 100 | ND |
| 9 | 14-0166* | 50 | 50 | | | | 100 | P |
| 10 | 15-0074 | 30 | 70 | | | | 100 | ND |
| 11 | 15-0240 | 30 | 70 | | | | 100 | ND |
| 12 | 12-0246* | 20 | 80 | | | | 100 | R |
| 13 | 13-0102* | 20 | 80 | | | | 100 | R |
| 14 | 13-0306 | 20 | 80 | | | | 100 | ND |
| 15 | 15-0046 | 20 | 80 | | | | 100 | R |
| 16 | 10-0280 | 10 | 90 | | | | 100 | ND |
| 17 | 15-0121 | 10 | 40 | 10 | | | 100 | ND |
| 18 | 13-0127 | 50 | 30 | 20 | | | 100 | R |
| 19 | 10-0021 | 30 | 30 | 40 | | | 100 | ND |
| 20 | 15-0233 | 20 | 60 | 20 | | | 100 | ND |
| 21 | 10-0005 | 50 | | 50 | | | 100 | P |
| 22 | 10-0284* | | 100 | | | | 100 | R |
| 23 | 11-0242 | | 100 | | | | 100 | R |
| 24 | 13-0199 | | 100 | | | | 100 | R |
| 25 | 14-0133 | | 100 | | | | 100 | R |
| 26 | 15-0001 | | 100 | | | | 100 | R |
| 27 | 14-0143 | | 95 | | | 5 | 100 | ND |
| 28 | 07-0663 | | 90 | | | 10 | 100 | ND |
| 29 | 14-0012* | | 90 | | | 10 | 100 | ND |
| 30 | 12-0268 | | 90 | | | 20 | 100 | ND |
| 31 | 14-0052* | | 80 | | | 20 | 100 | ND |
| 32 | 14-0158* | | 70 | | | 30 | 100 | ND |
| 33 | 15-0116* | | 70 | | | 30 | 100 | ND |
| 34 | 12-0284 | | 90 | 10 | | | 100 | R |
| 35 | 13-0301 | | 90 | 10 | | | 100 | ND |
| 36 | 15-0239 | | 90 | 10 | | | 100 | ND |
| 37 | 15-0274 | | 90 | 10 | | | 100 | ND |
| 38 | 11-0236 | | 80 | 20 | | | 100 | R |
| 39 | 11-0195 | | 60 | 40 | | | 100 | R |
| 40 | 15-0168 | | 60 | 40 | | | 100 | R |
| 41 | 12-0103 | | 50 | 50 | | | 100 | ND |
| 42 | 13-0182 | | 50 | 50 | | | 100 | R |
| 43 | 13-0269 | | 50 | 50 | | | 100 | ND |
| 44 | 13-0154 | | 50 | 50 | | | 100 | ND |
| 45 | 15-0038 | | 30 | 70 | | | 100 | ND |
| 46 | 16-0057 | | 20 | 80 | | | 100 | ND |
| 47 | 15-0181* | | 20 | 80 | | | 100 | ND |
| 48 | 12-0271 | | 20 | 80 | | | 100 | R |
| 49 | 09-0634 | | 10 | 90 | | | 100 | ND |
| 50 | 10-0130* | | 5 | 95 | | 10 | 100 | R |
| 51 | 10-0001* | | | 100 | | 10 | 100 | ND |
| 52 | 10-0272* | | | 100 | 10 | 20 | 100 | R |
| 53 | 13-0267* | | | 90 | 20 | 10 | 100 | R |
| 54 | 15-0152* | | | 90 | | | 100 | ND |
| 55 | 12-0215 | | | 80 | | | 100 | R |
| 56 | 14-0187* | | 90 | | | | 100 | R |
| 57 | 10-0190 | | 80 | | | | 100 | R |
| 58 | 15-0167 | | | 90 | | 10 | 100 | R |
| 59 | 12-0358* | | 90 | | | 30 | 100 | ND |
| 60 | 15-0089 | | 70 | 40 | | 60 | 100 | R |
| 61 | 13-0149* | | | 40 | | 100 | 100 | R |
| 62 | 15-0050 | | | | | | 100 | ND |
| 63 | 15-0013* | | | | | | 100 | R |
| 64 | RAJI * | | | | | | 100 | n/a |

SEQUENCE LISTING

```
<160> NUMBER OF SEQ ID NOS: 6

<210> SEQ ID NO 1
<211> LENGTH: 417
<212> TYPE: PRT
<213> ORGANISM: Homo sapiens

<400> SEQUENCE: 1

Met Ala Arg Ala Met Ala Ala Ala Trp Pro Leu Leu Leu Val Ala Leu
1               5                   10                  15

Leu Val Leu Ser Trp Pro Pro Pro Gly Thr Gly Asp Val Val Val Gln
            20                  25                  30

Ala Pro Thr Gln Val Pro Gly Phe Leu Gly Asp Ser Val Thr Leu Pro
        35                  40                  45

Cys Tyr Leu Gln Val Pro Asn Met Glu Val Thr His Val Ser Gln Leu
    50                  55                  60

Thr Trp Ala Arg His Gly Glu Ser Gly Ser Met Ala Val Phe His Gln
65                  70                  75                  80
```

```
Thr Gln Gly Pro Ser Tyr Ser Glu Ser Lys Arg Leu Glu Phe Val Ala
                85                  90                  95

Ala Arg Leu Gly Ala Glu Leu Arg Asn Ala Ser Leu Arg Met Phe Gly
            100                 105                 110

Leu Arg Val Glu Asp Glu Gly Asn Tyr Thr Cys Leu Phe Val Thr Phe
            115                 120                 125

Pro Gln Gly Ser Arg Ser Val Asp Ile Trp Leu Arg Val Leu Ala Lys
            130                 135                 140

Pro Gln Asn Thr Ala Glu Val Gln Lys Val Gln Leu Thr Gly Glu Pro
145                 150                 155                 160

Val Pro Met Ala Arg Cys Val Ser Thr Gly Gly Arg Pro Pro Ala Gln
                165                 170                 175

Ile Thr Trp His Ser Asp Leu Gly Gly Met Pro Asn Thr Ser Gln Val
                180                 185                 190

Pro Gly Phe Leu Ser Gly Thr Val Thr Val Thr Ser Leu Trp Ile Leu
                195                 200                 205

Val Pro Ser Ser Gln Val Asp Gly Lys Asn Val Thr Cys Lys Val Glu
210                 215                 220

His Glu Ser Phe Glu Lys Pro Gln Leu Leu Thr Val Asn Leu Thr Val
225                 230                 235                 240

Tyr Tyr Pro Pro Glu Val Ser Ile Ser Gly Tyr Asp Asn Asn Trp Tyr
                245                 250                 255

Leu Gly Gln Asn Glu Ala Thr Leu Thr Cys Asp Ala Arg Ser Asn Pro
                260                 265                 270

Glu Pro Thr Gly Tyr Asn Trp Ser Thr Thr Met Gly Pro Leu Pro Pro
                275                 280                 285

Phe Ala Val Ala Gln Gly Ala Gln Leu Leu Ile Arg Pro Val Asp Lys
290                 295                 300

Pro Ile Asn Thr Thr Leu Ile Cys Asn Val Thr Asn Ala Leu Gly Ala
305                 310                 315                 320

Arg Gln Ala Glu Leu Thr Val Gln Val Lys Glu Gly Pro Pro Ser Glu
                325                 330                 335

His Ser Gly Met Ser Arg Asn Ala Ile Ile Phe Leu Val Leu Gly Ile
                340                 345                 350

Leu Val Phe Leu Ile Leu Leu Gly Ile Gly Ile Tyr Phe Tyr Trp Ser
                355                 360                 365

Lys Cys Ser Arg Glu Val Leu Trp His Cys His Leu Cys Pro Ser Ser
                370                 375                 380

Thr Glu His Ala Ser Ala Ser Ala Asn Gly His Val Ser Tyr Ser Ala
385                 390                 395                 400

Val Ser Arg Glu Asn Ser Ser Ser Gln Asp Pro Gln Thr Glu Gly Thr
                405                 410                 415

Arg
```

<210> SEQ ID NO 2
<211> LENGTH: 19
<212> TYPE: PRT
<213> ORGANISM: Homo sapiens

<400> SEQUENCE: 2

```
Ala Arg Cys Val Ser Thr Gly Gly Arg Pro Pro Ala Gln Ile Thr Trp
1               5                   10                  15

His Ser Asp
```

```
<210> SEQ ID NO 3
<211> LENGTH: 17
<212> TYPE: PRT
<213> ORGANISM: Homo sapiens

<400> SEQUENCE: 3

Arg Cys Val Ser Thr Gly Gly Arg Pro Pro Ala Gln Ile Thr Trp His
1               5                   10                  15
Ser

<210> SEQ ID NO 4
<211> LENGTH: 15
<212> TYPE: PRT
<213> ORGANISM: Homo sapiens

<400> SEQUENCE: 4

Cys Val Ser Thr Gly Gly Arg Pro Pro Ala Gln Ile Thr Trp His
1               5                   10                  15

<210> SEQ ID NO 5
<211> LENGTH: 13
<212> TYPE: PRT
<213> ORGANISM: Homo sapiens

<400> SEQUENCE: 5

Val Ser Thr Gly Gly Arg Pro Pro Ala Gln Ile Thr Trp
1               5                   10

<210> SEQ ID NO 6
<211> LENGTH: 11
<212> TYPE: PRT
<213> ORGANISM: Homo sapiens

<400> SEQUENCE: 6

Ser Thr Gly Gly Arg Pro Pro Ala Gln Ile Thr
1               5                   10
```

DETECTION OF CD-155, THE POLIOVIRUS RECEPTOR

RELATED APPLICATION DATA

This application is a national stage filing under 35 U.S.C. 371 of International Application No. PCT/US2017/054733, filed Oct. 2, 2017, which claims the benefit of priority of U.S. Patent Application Ser. No. 62/404,945, filed Oct. 6, 2016, both of which are expressly incorporated herein by reference in their entirety.

STATEMENT OF GOVERNMENT INTERESTS

This invention was made with government support under 5R35CA197264 awarded by the National Cancer Institute. The government has certain rights in the invention.

TECHNICAL FIELD OF THE INVENTION

This invention is related to the area of immunotherapy. In particular, it relates to any assay to test for a receptor for immunotherapy.

BACKGROUND OF THE INVENTION

Malignant gliomas comprise a family of highly aggressive brain tumors with glioblastoma representing the most frequent and most malignant type. Median survival for newly diagnosed glioblastoma with the current standard of care, including maximum safe surgical resection, radiotherapy, and concomitant chemotherapy with temozolomide, is 14.6 months.[1] The modest survival improvement achieved with currently approved therapies is plagued by systemic toxicities and a poor health-related quality of life. Hence, there is a dire need for the development of new therapeutics to improve glioblastoma patient survival. PVSRIPO, a recombinant, non-pathogenic human poliovirus (PV) vaccine is showing promise in clinical trials for glioblastoma. This approach takes advantage of the marked tropism of PV for solid cancers mediated by natural ectopic over-expression of the human PV receptor, CD155, on the surface of neoplastic cells.[2] PVSRIPO infection and killing of cancer cells initiates a broad range of pro-inflammatory and immunogenic events that may recruit adaptive immune effector responses against the tumor.[3]

CD155, also known as the PV Receptor (PVR) or Nectin-like molecule 5 (Necl-5), is a cell adhesion molecule of the immunoglobulin (Ig) superfamily.[4] Functional CD155 is a 417 amino acid (aa) membrane-anchored glycoprotein consisting of a putative signal peptide (1-20 aa), an extracellular domain with 3 Ig-like loops (D1-3; 21-343 aa), a transmembrane domain (344-367 aa), and a cytoplasmic domain (368-417 aa).[5,6] D1 resembles an Ig-variable domain, while D2 and 3 are similar to Ig-constant domains. CD155 is heavily glycosylated at 8 putative glycosylation sites in D1-3.[6,7] Alternative splicing of CD155 mRNA yields CD155-α/δ, membrane-bound forms that differ only in their C-terminal cytoplasmic domains; CD155-β/γ lack transmembrane domains and are secreted.[8,9] PV binds to the D1 loop of the CD155 glycoprotein.[10-12]

Despite its role as a key pathogenic factor in paralytic poliomyelitis, CD155's distribution in the normal primate organism remains uncertain. In humans/chimpanzees, only gastrointestinal (GI) epithelium, GI-associated lymphatic tissues and spinal cord are sites of significant PV propagation (implying CD155 expression).[13-14] There is scant immunohistochemistry (IHC) evidence for CD155 expression in primates, except a study in the GI tract, matching CD155 expression to known sites of PV replication.[15] There also is some evidence for PV presence in myeloid cells expressing CD155 (macrophages, dendritic cells)[16-17] and in vascular endothelial cells[16] of infected primates, although these cells are not significant reservoirs for PV propagation in vivo. The main reason for an incomplete understanding of CD155 distribution is the lack of antibodies suitable for IHC (see Results).

Many IHC studies yielded evidence for broad, ectopic CD155 upregulation in many cancer histotypes,[3,4] albeit with immunologic probes used in assays that were not vetted in normal tissues in parallel. But up until now there has been no reliable method for unambiguous, semi-quantitative analysis of CD155 expression in routinely available patient tumor tissue samples. We sought to validate our assay by including IHC for CD155 in known sites of PV replication/CD155 expression and excluding it in confirmed negative controls. There is a continuing need in the art to have a reliable assay for this important cellular target.

SUMMARY OF THE INVENTION

According to one aspect of the invention a method of assaying CD155 expression in a tumor tissue sample is provided. A tumor tissue sample is contacted under conditions suitable for antibody-antigen binding with a primary antibody that specifically binds to an epitope on CD155. The epitope is in residues 164-182 of CD155.

According to another aspect of the invention a method of assaying CD155 expression in a tumor tissue sample is provided. A tumor tissue sample is contacted under conditions suitable for antibody-antigen binding with rabbit monoclonal antibody D3G7H.

Another aspect of the invention is an antigen-antibody complex comprising CD155 and an antibody that specifically binds to an epitope on CD155. The epitope is in residues 164-182 of CD155. The CD155 in the antigen-antibody complex is in a tumor tissue sample.

Still another aspect of the invention is an antigen-antibody complex comprising

CD155 and antibody D3G7H. The antibody specifically binds to an epitope on CD155. The epitope comprises residue 172 of CD155. The CD155 in the antigen-antibody complex is in a tumor tissue sample.

These and other embodiments which will be apparent to those of skill in the art upon reading the specification provide the art with methods for determining expression of CD155 in tissues and intermediate products of the assay.

BRIEF DESCRIPTION OF THE DRAWINGS

FIGS. 1A-1I. Validation of anti-CD155 mAb D3G7H in tissues with known CD155 status. FIG. 1B shows antibody D3G7H IHC in Raji xenograft and FIG. 1D shows staining in human tonsil. FIGS. 1C, 1E, 1G show the corresponding assays with isotype-matched non-specific lgG control. Figs. H., I show antibody D3G7H IHC in the primate spinal cord anterior horn. CD 155-positive staining in anterior horn motor neurons (FIG. 1H; arrows); there was no staining in corresponding isotype-matched non-specific lgG controls (FIG. 1I; arrows).

FIGS. 2A-2E. CD155 expression in glioblastoma. FIG. 2A shows a table summarizing CD155 expression scores in 62 glioblastomas, one small cell glioblastoma (line no. 12) and in Raji xenograft tissue (line no. 64) with anti-CD155 mAb D3G7H IHC (see Example 1 for scoring method). Endothelial staining was scored separately. Tumor status is referred to as newly diagnosed (ND), recurrent (R) or progressive (P). Asterisks mark tumor samples that were analyzed by immunoblot in parallel (FIG. 2F). FIGS. 2B-2E show examples of glioblastoma immunohistochemistry (IHC) with Isotype-matched, non-specific IgG control (FIG. 2B) or anti-CD 155 mAb D3G7H IHC (FIGS. 2C-2E) demonstrating 3+ endothelial staining (FIG. 2C), 2+ tumor staining (FIG. 2D) and 3+ tumor staining (FIG. 2E) in glioblastoma cells. In each case, 3+ endothelial cell staining served as the internal positive control; numbers below the panels indicate the case number (see FIG. 2A). FIG. 2A indicates the case number for each line number.

FIGS. 3A-3C show CD 155 expression levels do not correlate with susceptibility to, propagation of, and cancer cell killing by PVSRIPO.

A sequence listing forms part of this disclosure.

DETAILED DESCRIPTION OF THE INVENTION

The inventors have developed a robust assay which can detect CD155 in tissue samples. The assay employs an antibody which recognizes an epitope on the extracellular portion of the protein. The epitope includes arginine residue 172. The sequence of full length CD155 is shown in SEQ ID NO: 1 for the alpha isoform. Sequences of CD155 that contain the epitope are shown in SEQ ID NO: 2-6. While antibodies to other epitopes may be used, no other antibodies tested were found to be specifically reactive to tumor tissue.

In some embodiments the primary antibody that is reactive with CD155 is itself labeled. Such labeling can employ any labeling means known in the art, including but not limited to a radiolabel, a fluorescent label, and enzymatic label, an antigenic tag. Alternatively, the primary antibody can be indirectly detected using a secondary antibody which specifically binds to the primary antibody. Typically, such secondary antibodies are directed to constant regions of the primary antibody. The secondary antibody may be labeled, directly or indirectly. A chromogenic substrate may be used to develop a color from an appropriately labelled or conjugated antibody. Typical chromogenic substrates include ABTS, OPD, AmplexRed, Homovanilic acid, Luminol, TMB, AEC, AP, and DAB.

Antibodies which react with an appropriate epitope may be, for example, monoclonal or polyclonal, murine, camelid, or rabbit. The antibodies may be human, humanized, or chimeric. These listings are exemplary rather than exhaustive.

Tissues which can be used for testing may be fixed or frozen, for example. In some cases the samples may have been preserved and may need to be treated to remove preservatives. For example, a sample may be de-paraffinized using xylene or hot water. Similarly, the sample may need to be treated to activate, expose, or unblock an important epitope. These steps are encompassed and contemplated by the present invention, without limitations.

The type of tumor tissue which may be assayed is without limitation. The tumors may be brain tumors or other types of tumors. If a brain tumor, the tumor type may be any of medulloblastoma, atypical teratoid rhabdoid tumor (ATRT), primitive neuroectodermal tumor (PNET), meningioma, anaplastic ependymoma, and pleomorphic xanthoastrocytoma (PXA). If the type of tumor is not a brain tumor it may be, without limitation, a cancer selected from the group consisting of acute lymphoblastic leukemia, acute myeloid leukemia, adrenocortical carcinoma, AIDS-related lymphoma, anal cancer, appendix cancer, grade I (anaplastic) astrocytoma, grade II astrocytoma, grade III astrocytoma, grade IV astrocytoma, atypical teratoid/rhabdoid tumor of the central nervous system, basal cell carcinoma, bladder cancer, breast cancer, breast sarcoma, bronchial cancer, bronchoalveolar carcinoma, Burkitt lymphoma, cervical cancer, chronic lymphocytic leukemia, chronic myelogenous leukemia, colon cancer, colorectal cancer, craniopharyngioma, cutaneous T-cell lymphoma, endometrial cancer, endometrial uterine cancer, ependymoblastoma, ependymoma, esophageal cancer, esthesioneuroblastoma, Ewing's sarcoma, extracranial germ cell tumor, extragonadal germ cell tumor, extrahepatic bile duct cancer, fibrous histiocytoma, gallbladder cancer, gastric cancer, gastrointestinal carcinoid tumor, gastrointestinal stromal tumor, gestational trophoblastic tumor, gestational trophoblastic tumor, glioma, hairy cell leukemia, head and neck cancer, heart cancer, hepatocellular cancer, Hilar cholangiocarcinoma, Hodgkin's lymphoma, hypopharyngeal cancer, intraocular melanoma, islet cell tumor, Kaposi sarcoma, Langerhans cell histiocytosis, large-cell undifferentiated lung carcinoma, laryngeal cancer, lip cancer, lung adenocarcinoma, lymphoma, macroglobulinemia, malignant fibrous histiocytoma, medulloblastoma, medulloepithelioma, melanoma, Merkel cell carcinoma, mesothelioma, endocrine neoplasia, multiple myeloma, mycosis fungoides, myelodysplasia, myelodysplastic/myeloproliferative neoplasms, myeloproliferative disorders, nasal cavity cancer, nasopharyngeal cancer, neuroblastoma, non-Hodgkin's lymphoma, oral cancer, oropharyngeal cancer, osteosarcoma, ovarian clear cell carcinoma, ovarian epithelial cancer, ovarian germ cell tumor, pancreatic cancer, papillomatosis, paranasal sinus cancer, parathyroid cancer, penile cancer, pharyngeal cancer, pineal parenchymal tumor, pineoblastoma, pituitary tumor, plasma cell neoplasm, plasma cell neoplasm, pleuropulmonary blastoma, primary central nervous system lymphoma, prostate cancer, rectal cancer, renal cell cancer, respiratory tract cancer with chromosome 15 changes, retinoblastoma, rhabdomyosarcoma, salivary gland cancer, Sézary syndrome, small cell lung cancer, small intestine cancer, soft tissue sarcoma, squamous cell carcinoma, squamous non-small cell lung cancer, squamous neck cancer, supratentorial primitive neuroectodermal tumor, supratentorial primitive neuroectodermal tumor, testicular cancer, throat cancer, thymic carcinoma, thymoma, thyroid cancer, cancer of the renal pelvis, urethral cancer, uterine sarcoma, vaginal cancer, vulvar cancer, Waldenstrom macroglobulinemia, and Wilms tumor.

The technique used for detection of antibody binding is dependent on the type of label or detectable moiety which is used. Some detection may be simply by visual observation. Some may be by using a spectrophotometer or a fluorescence microscope. Others may use a radiographic film or a scintillation counter. Binding may be scored by an experienced pathologist. Preferably scoring will be done in a blinded fashion, i.e., with the identity of the samples coded.

When the antibody for CD155 binds to CD155 in a tissue, it forms a complex in or on the tissue. This is sometimes called an immune complex. The binding of the antibody to the tissue can be used to indicate the percentage of cells in the tumor that express CD155. The binding can be used to determine where in the cell the CD155 is located. The binding can be used to determine in what portions of a tumor CD155 is expressed.

Kits may be used to provide key ingredients for running the assay. These typically include a primary and secondary antibody. The kits may also include stains or reagents for developing detectable moieties on the secondary antibody. The kits may include antigen retrieval agents, blocking agents, deparaffinization agents, reaction buffers, chromogenic substrates, and the like. Tools for handling tissue samples, such as knives, microtomes, scalpels, tweezers, microscope slides and the like may also be included. One typical deparaffinization agent which may be included is xylene. Kits are typically packaged in a unitary package, although subunits maybe separately packaged within the unitary package.

We have found that immunoblots cannot be used for patient sample analyses. Applicants do not wish to be bound by any theory of operation, however, it appears that tumor tissues contain components (such as myeloid cells and endothelial cells) that express low levels of CD155. An immunoblot cannot distinguish between a positive CD155 signal derived from myeloid and/or endothelial cells and a positive DC155 signal derived from tumor cells. Because immunohistochemistry retains the architecture of the tumor tissue, signals from the myeloid and/or endothelial cells and from tumor cells are spatially distinguishable.

CD155 is the founding member of the nectin family of cell adhesion molecules.[4] Of the nectin family members, CD155 and CD112 have gained particular attention due to their emerging roles in modulation of the innate immune response to infection, in tumor immunobiology, and as receptors for oncolytic viruses under clinical investigation (CD112 is a receptor for α-herpesviruses).[30] CD112 and CD155 are ligands for the activating receptor CD226 (DNAM-1) present on natural killer (NK) cells,[31] but also interact with inhibitory checkpoint molecules CD96 and T cell immunoreceptor with ImmunoGlobulin and ITim domains (TIGIT).[32] This places CD155 at the center of a regulatory system with decisive roles in the innate defense against transformed or infected cells.[32]

In this context, widespread ectopic CD155 expression in solid neoplasia is of interest. The mechanisms of CD155 upregulation in cancer are poorly understood; transcriptional induction of the CD155 gene has been linked to disruption of tissue architecture with injury or malignant transformation[33] or with the DNA-damage response.[34] Also, the immunobiological significance of CD155 expression in neoplasia is unknown. Instances of both, suppression[35] and stimulation[36] of immune effector functions were linked to CD155 upregulation in neoplastic cells. CD155 downregulation occurring with DNA/retrovirus infection has been interpreted as a mechanism of immune evasion.[37,38]

CD155 expression in glioblastoma cells renders them susceptible to PV infection and killing, an indispensible aspect of PVSRIPO oncolytic immunotherapy.[2] In our report, we provide details for a robust, reliable and specific IHC method for detecting CD155 in FFPE tumor tissue sections based on a commercially available anti-CD155 antibody with unprecedented specificity. Our studies corroborate earlier evidence for an association of CD155 with glioblastoma,[2,20] extend these initial findings to indicate virtually universal expression in glioblastoma, and confirm similar systematic analyses reaching the same conclusions in other cancer histotypes with different techniques, e.g., FACS analyses in melanoma.[39] Studies correlating CD155 expression levels in clonal cell populations with PVSRIPO susceptibility indicated that even marginal CD155 expression levels (determined by immunoblot or qFACS), mediate full susceptibility to viral infection and cell killing. Availability of a robust IHC assay for detecting CD155 will enable pre-clinical assessments of the suitability of PVSRIPO oncolytic immunotherapy in cancers other than glioblastoma.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Study Population, Patient Tumor Tissues, and Vertebrate Animal Tissues

De-identified archival tissue samples, 62 glioblastoma/1 giant cell glioblastoma (Table 1), were obtained with IRB approval from the Preston Robert Tisch Brain Tumor Center Biorepository at Duke University Medical Center (DUMC). Cases were selected from archived Formalin-Fixed, Paraffin-Embedded (FFPE) or cryogenic tumor blocks stemming from resected tissue. The material consisted of representative FFPE glioblastoma sections, of which 34, 27, and 2 were from surgeries for newly diagnosed, recurrent or progressive disease, respectively, at DUMC (Table 1). The study population included 34 males and 29 females (primarily of Caucasian descent; n=62), that were 24-82 yrs of age (average 57 yrs) at the time of resection. Tissue blocks were selected by a DUMC neuropathologist as ~80-100% viable tumor and >1 cm$^2$ of tissue by light microscopic examination of Hematoxylin and Eosin (H&E) stained sections. Serial unstained sections were cut from these FFPE and frozen blocks and stained for CD155 by immunohistochemistry (IHC) or immunoblot, respectively. Raji cells (ATCC, Cat. No. CCL-86) were used to initiate subcutaneous tumors in athymic Balb/c mice as described before;[18] resected Raji tumor tissue was processed to obtain FFPE sections. Spinal cord homogenates were surplus tissues from euthanized wt and CD155-transgenic C57B16 mice, respectively. Institutional guidelines regarding animal experimentation were followed.

TABLE 1

Patient characteristics

| | |
|---|---|
| Total number of Patients | 63 (62 glioblastoma, 1 small cell glioblastoma) |

Gender:

| | |
|---|---|
| Male | 34 (54%) |
| Female | 29 (46%) |

Age:

| | |
|---|---|
| ≤45 years | 11 (17.5%) |
| >45 years | 52 (82.5%) |

Tumor Status:

| | |
|---|---|
| Newly Diagnosed | 34 (54%) |
| Recurrent | 27 (43%) |
| Progressed | 2 (3%) |

Immunohistochemistry, Histopathology, Scoring, Immunofluorescence (IF), and Immunoblot Serial FFPE sections (5 micron thickness) were stained for CD155 using automated IHC techniques on a Bond™-maX Processing Module (Leica Microsystems, Buffalo Grove, Ill.), utilizing the Bond™ Polymer Refine Detection kit (Leica Microsystems, Cat. No. DS9800). FFPE sections were deparaffinized, hydrated with alcohol and subjected to heat-induced epitope retrieval with Bond Epitope Retrieval Solution 1 (citrate buffer, pH 6.0; Leica Microsystems, Cat. No. AR9961). Slides were then washed with bond wash solution (Leica Microsystems, Cat. No. AR9590) and exposed to peroxide block (10 min). The sections were sequentially blocked with Fc receptor blocker (Innovex Biosciences, Richmond, Calif., Cat. No. NB309) (45 min) and protein block (Leica Microsystems, Cat. No. RE7102-CE) (30 min). We used the following anti-CD155 antibodies: rabbit polyclonal (aa314-342) IHC-plus™ (LSBio Cat. No. LS-B10536); mouse monoclonal antibody (mAb) (Biolegend Cat. No. 337602); rabbit polyclonal (Novus Cat. No. NBP1-02520); rabbit mAb (Cell Signaling Technology, Cat. No. 13544); D171,[19] and D480.[20] Anti-CD155 antibody was applied to the tissue sections at a concentration of 5 μg/mL (60 min). Sections were then treated sequentially with polymer (8 min), mixed DAB refine (10 min), and hematoxylin solutions (5 min). CD155 expression was defined as membranous and cytoplasmic staining on tumor cells and endothelial cells. The histologic sections were scored for IHC intensity by a neuropathologist (REM) using the criteria described for evaluating HER2 expression in breast cancer,[21] where scores indicate the intensity of staining as follows: 0, no staining; 1+, weak reactivity in ≤10% of cells; 2+, weak to moderate reactivity in >10% of cells; and 3+, strong reactivity in ≥30% of cells. CD155 IF on tonsil FFPE sections was performed using the PerkinElmer Opal kit (PerkinElmer, Shelton, Conn., Cat. No. NEL796001KT) following the manufacturer's instructions. Briefly, the slides were deparaffinized, rehydrated in ethanol and antigen retrieval was performed in Target Antigen Retrieval buffer AR9 (PerkinElmer, Cat. No. AR900250ML) using microwave incubation. Rabbit mAb (Cell Signaling Technology, Cat. No. 13544) or rabbit (DA1E) isotype control (Cell Signaling Technology, Cat. No. #3900) antibodies were applied to sections at a concentration of 1 μg/mL (30 min) in a humidified chamber at room temperature. Sections were then incubated in secondary antibody working solution (Perkin Elmer, Cat. No. ARH1001EA) (10 min) at room temperature. Visualization of CD155 was accomplished using Opal 570 (1:50), after which the slides were placed in AR9 buffer and heated using microwave incubation. Nuclei were subsequently stained with 4',6-diamidino-2-phenylindole solution (Perkin Elmer, Cat. No. NEL796001KT), and the sections were cover slipped using Vectashield HardSet Antifade mounting media (Vector Laboratories, Burlingame, Calif., Cat. No. H-1200). The slides were scanned using the Vectra 3.0 System; image analysis was performed using the InForm image analysis software (both PerkinElmer). For immunoblot, frozen tissue sections (50 micron thickness), from each tumor were treated with the appropriate volume of T-PER Tissue Protein Extraction Reagent (Life Technologies Corporation, Carlsbad, Calif., Cat. No. 78510), and subjected to homogenization. Total protein concentration was determined by Bradford method and 30 μg of protein (per sample) was subjected to SDS-PAGE and immunoblot as described previously.[22]

PVSRIPO, CD155-Expressing Murine Cell Lines, and Quantitative FACS Analysis

Derivation, propagation and purification of PVSRIPO, and PVSRIPO infection procedures were described elsewhere.[23] TRAMP-C2 cells (ATCC, Cat. No. CRL-2731) were transduced by transfection with the pSVL-H2OA CD155 expression plasmid (a gift of Dr. E. Wimmer)[6] and clonally selected as described before.[23] CD155 numbers on the surface of transduced TRAMP-C2 cells were determined by quantitative FACS (qFACS), using the Quantum Simply Cellular anti-Mouse IgG kit (Bangs Laboratories, Inc., Fishers, Ind.) as described previously.[24] Briefly, a cocktail of uniform size beads, one blank and four with varying capacities to bind mouse IgG, and the cells were stained with 10 μg/mL of mouse IgG1-AF488 (Isotype Control Ab) and D171-AF488 (CD155-specific Ab) at 4° C. (45 min). After washing, the beads and the cells were analyzed on a Becton Dickinson FACSCalibur instrument. Analysis of receptor density was performed by interpolation with the bead standard curves using QuickCal analysis software provided with the kit.

EXAMPLE 2

CD155 is emerging as a molecule of central interest in tumor immunology and as a therapeutic target in cancer immunotherapy, e.g., oncolytic immunotherapy agent PVSRIPO.[20] Thus, developing reliable methods to determine CD155 expression in routinely available patient samples is an urgent priority.

Validating Anti-CD155 Antibody D3G7H

In the past, reliable CD155 detection by immunoblot or IHC has been hampered by the lack of suitable antibodies. The first anti-CD155 antibody generated (D171), a mouse mAb raised against fractionated HeLa cell membranes,[19] led to the identification of CD155 as the PV receptor[6] by virtue of its ability to block PV infection. D171, however, poorly recognizes denatured CD155 and exhibits profuse non-specific staining (e.g. in immunoblot)[25] and, hence, is unsuitable for IHC in FFPE materials. To address this shortcoming, we previously developed a 2-step immunoblot protocol, immunoprecipitation of CD155 from non-denatured tumor homogenates with D171 mAb, followed by immunoblot with polyconal probes.[20] This procedure circumvented the limitations of D171 and eliminated non-specific background staining in CD155 immunoblots; however, this cumbersome and non-quantitative approach is not applicable for IHC.

To develop clinically viable IHC methods, we first conducted validation assays with a range of anti-CD155 antibodies in FFPE sections of confirmed positive and negative control tissues. These included assays in two tissues harboring confirmed sites of productive PV replication, tonsils and spinal cord,[13,14] and a human-derived tissue with confirmed CD155 absence, Raji cell xenografts (the CD155 gene is transcriptionally silenced in Epstein-Barr-Virus-infected lymphomas).[26] Our tests included antibodies D171, D480 (a rabbit polyclonal serum raised against the CD155 extracellular domain)[20] and several commercially available probes [rabbit polyclonal (aa314-342) IHC-plus™ (LSBio Cat. No. LS-B10536); mAb (Biolegend Cat. No. 337602); rabbit polyclonal (Novus Cat. No. NBP1-02520)]. Examination of IHC results in FFPE sections by the study pathologist (REM) revealed a lack of specificity of all tested antibodies, suggesting their unsuitability for a robust clinical assay (data not shown).

Figure 2B:
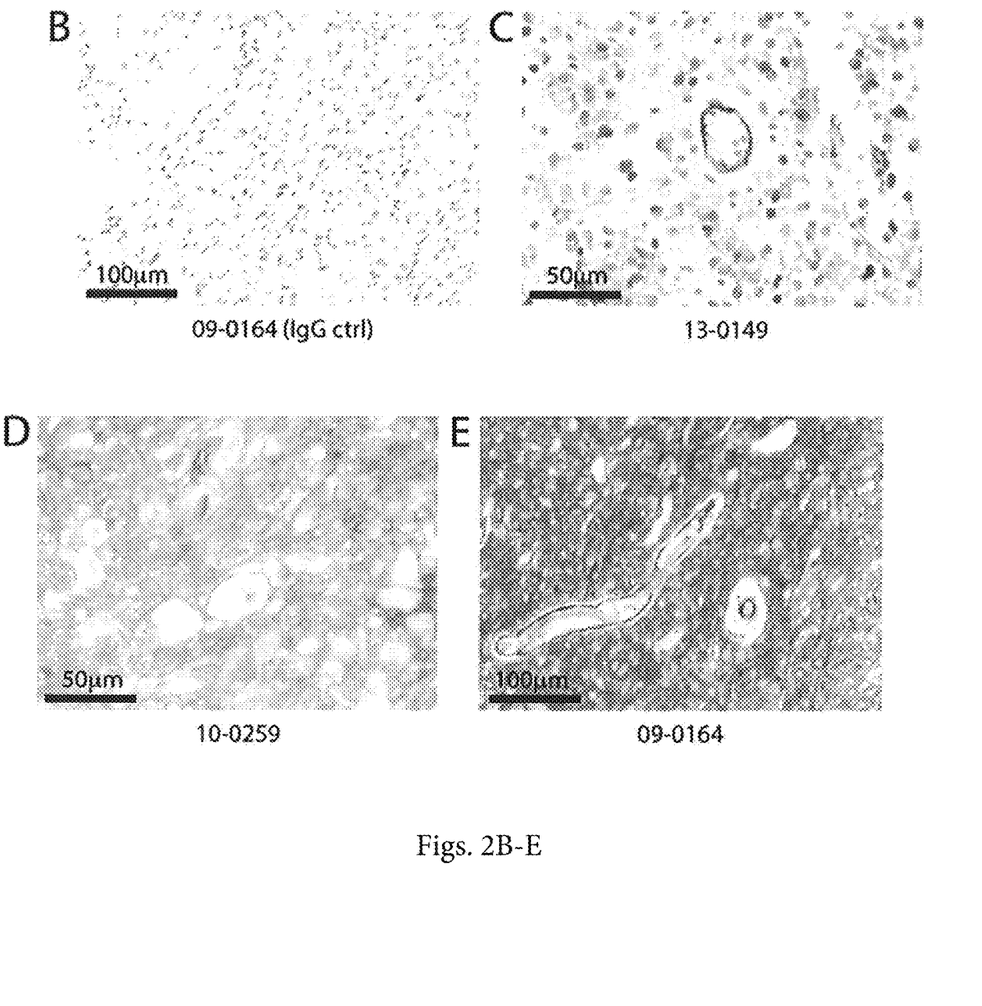
Figure 2F:
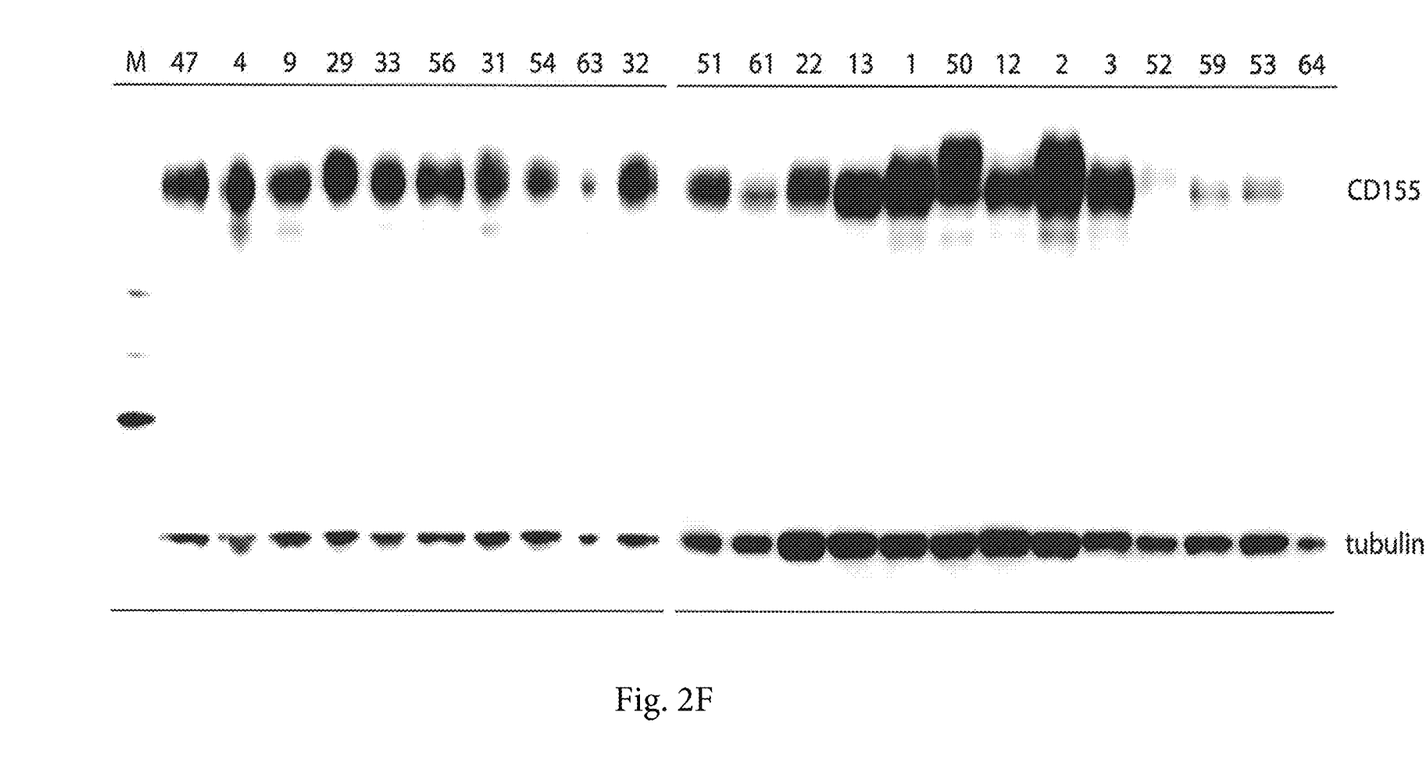
FIG. 2F shows a CD155 immunoblot with anti-CD155 mAb D3G7H in select glioblastoma samples and in Raji xenograft tissue (line 64). The numbers on top correspond to line numbers for individual cases.

Recently, a newly developed rabbit anti-CD155 mAb [Cell Signaling (D3G7H)] has demonstrated unprecedented specificity: immunoblot from spinal cord homogenates of CD155-transgenic mice revealed background-free staining for CD155 (FIG. 1A) and mono-specificity of the D3G7H probe was demonstrated for human tissues (FIG. 2F). Anti-CD155 mAb D3G7H did not exhibit positive staining in FFPE sections from Raji cell xenografts (FIGS. 1B, 1C), recapitulating the absence of non-specific reactivity observed in immunoblots in murine tissues (FIG. 1A) and in Raji xenografts (FIG. 2F). We observed staining for CD155 in FFPE human tonsil sections with D3(17171, both by IHC (FIGS. 1D, 1E) and by IF (FIGS. 1F, 1G) in a pattern matching a prior IF study with D171 in fresh-frozen sections from Rhesus macaque Peyer's patches.[15] CD155 was mainly present in cells located in the germinal centers (FIG. 1D-G).

Figure 1A:
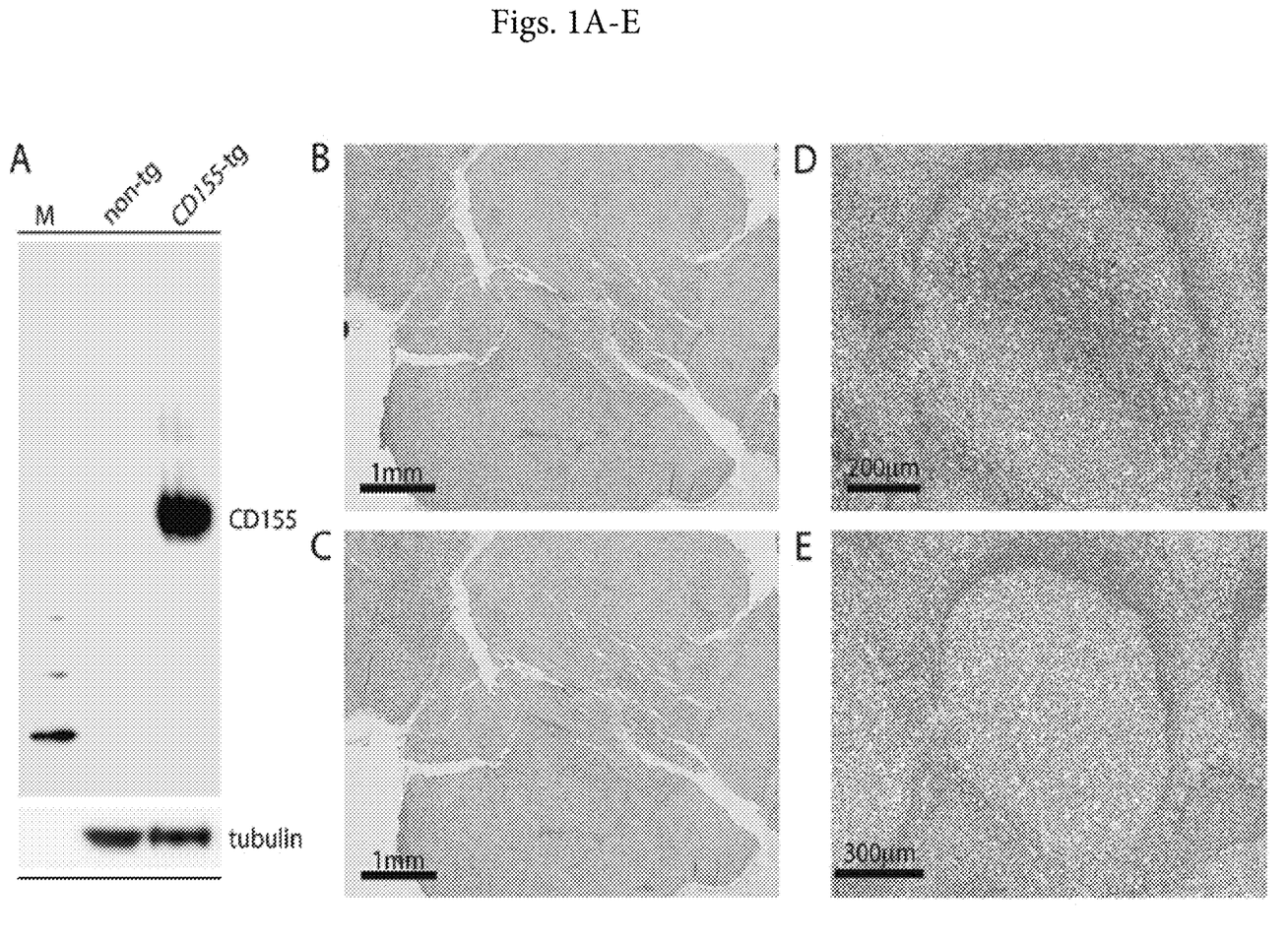
FIG. 1A: CD155 immunoblot in spinal cord homogenates from wt mice (non-tg) and CD155-transgenic mice (CDJ55-tg). Note the absence of non-specific staining.
Figure 1F:
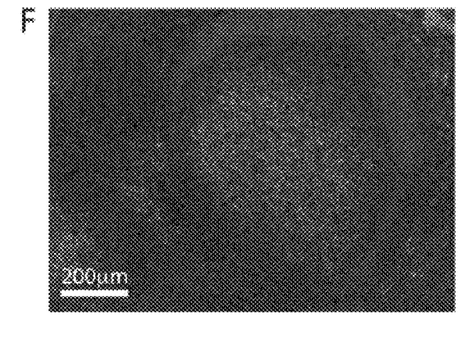
FIG. 1F shows immunofluorescence (IF) in human tonsil.
Figure 1G:
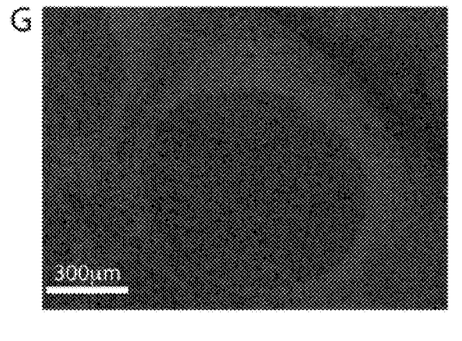
Figure 1H:
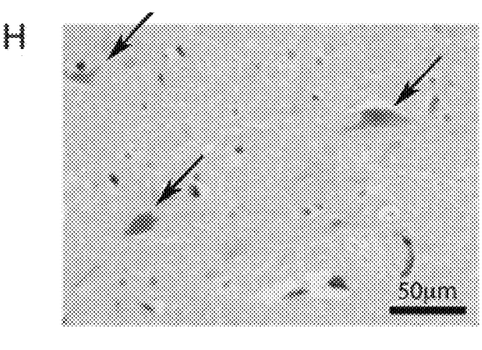
Figure 1I:
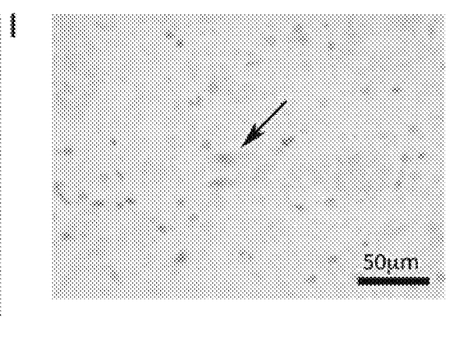

PV CNS infections are defined by specificity for lower motor neurons and flaccid paralysis is pathognomonic for poliomyelitis; accordingly, studies in mice transgenic for a CD155-promoter reporter suggested CD155 gene expression to be confined to the floor-plate/anterior horn/lower motor neuron compartment during embryonic development.[2] To the knowledge of these authors, successful CD155 IHC in the primate spinal cord has never been reported. We performed IHC with D3G7H in FFPE spinal cord tissues from Cynomolgus macaques, a WHO-standard primate species for evaluating PV neurovirulence. Cynomolgus macaques develop the clinical and histopathologic hallmarks of human paralytic poliomyelitis upon exposure to neurovirulent PVs.[27] Our tests revealed specific staining for CD155 in anterior horn motor neurons, consistent with the tropism and pathogenic profile of PV (FIGS. 1H, 1I). We also observed CD155 staining in normal CNS endothelial cells, in line with earlier observations of PV particles in CNS endothelial cells by electron microscopyl[16] and more recent mechanistic studies of CD155's involvement in trans-endothelial migration.[28] These data suggest that 1) D3G7H is mono-specific for human CD155 in immunoblot in murine tissues; 2) D3G7H is devoid of immune-reactivity in a confirmed CD155-negative human-derived tissue; 3) D3G7H detects CD155 in normal primate/human tissues known to support PV infection/replication; 4) D3G7H recognizes CD155 in cells that may not support productive PV replication (e.g., vascular endotheliurn), but execute physiologic functions associated with CD155 expression.

EXAMPLE 3

CD155 IHC in Glioblastomas

The positive validation of the anti-CD155 probe D3G7H described above, qualified it for 1HC tests in FFPE sections from glioblastoma patients. We evaluated CD155 expression in the tumor tissues of 63 patients with glioblastomas. In each case, the endothelial cells proved to exhibit 3+, dark brown stain product (FIG. 2A, C, E) and was used to compare the tumor cell reactivity with intermediate staining (2+ in 5% tumor; case no. 10-0259) (FIG. 2D) and dark brown staining (3+ in 95% tumor; case no. 09-0164) (FIG. 2E). Each case was evaluated for percentage positive cells (>2+ intensity) and negative cells (0-1+ reactivity). Necrotic regions were ignored. The immunoreactivity patterns in the tumors always demonstrated membranous staining (FIG. 2D), however, most tumors exhibited cells with prominent cytoplasmic staining as well (FIG. 2E). Nuclear reactivity was not noted. Overall, 49 (78%) cases demonstrated >50%, 2+ to 3+ reactivity by immunohistochemistry (FIG. 2A) and helped to delineate the cellular localization of the receptor in glioblastomas. Of note, only one case in this small series was considered to be negative for CD155 expression (FIG. 2A).

EXAMPLE 4

CD155 Immunoblot in Glioblastoma

To corroborate IHC findings, we performed immunoblot of 23 glioblastoma samples with the anti-CD155 probe D3G7H. As in immunoblot of murine tissues (FIG. 1A), we observed mono-specificity of D3G7H in human glioblastoma samples (FIG. 2F). Variable electrophoretic mobility of CD155 in distinct non-malignant tissues or individual tumors is commonly observed and is due to tissue type-specific glycosylation. Generally, CD155 levels determined by immunoblot correlated with IHC findings: e.g. when comparing high expressing cases (line numbers <10) with lower ones (line numbers >50). Definitive quantitative measurements of CD155 expression levels in patient tumor tissues should not be based on immunoblot data. A significant presence of CD155 in abundant non-malignant/stromal tumor components (vascular endothelium and macrophages) makes this unreliable, as stromal contents vary substantially individually (patient-to-patient) and intratumorally (sample-to-sample). For these reasons, we did not attempt to obtain quantitative measurements of CD155 expression in immunoblots or to correlate quantitative measurements with IHC data.

EXAMPLE 5

CD155 IHC as a Companion Diagnostic for PVSRIPO

Figure 3A:
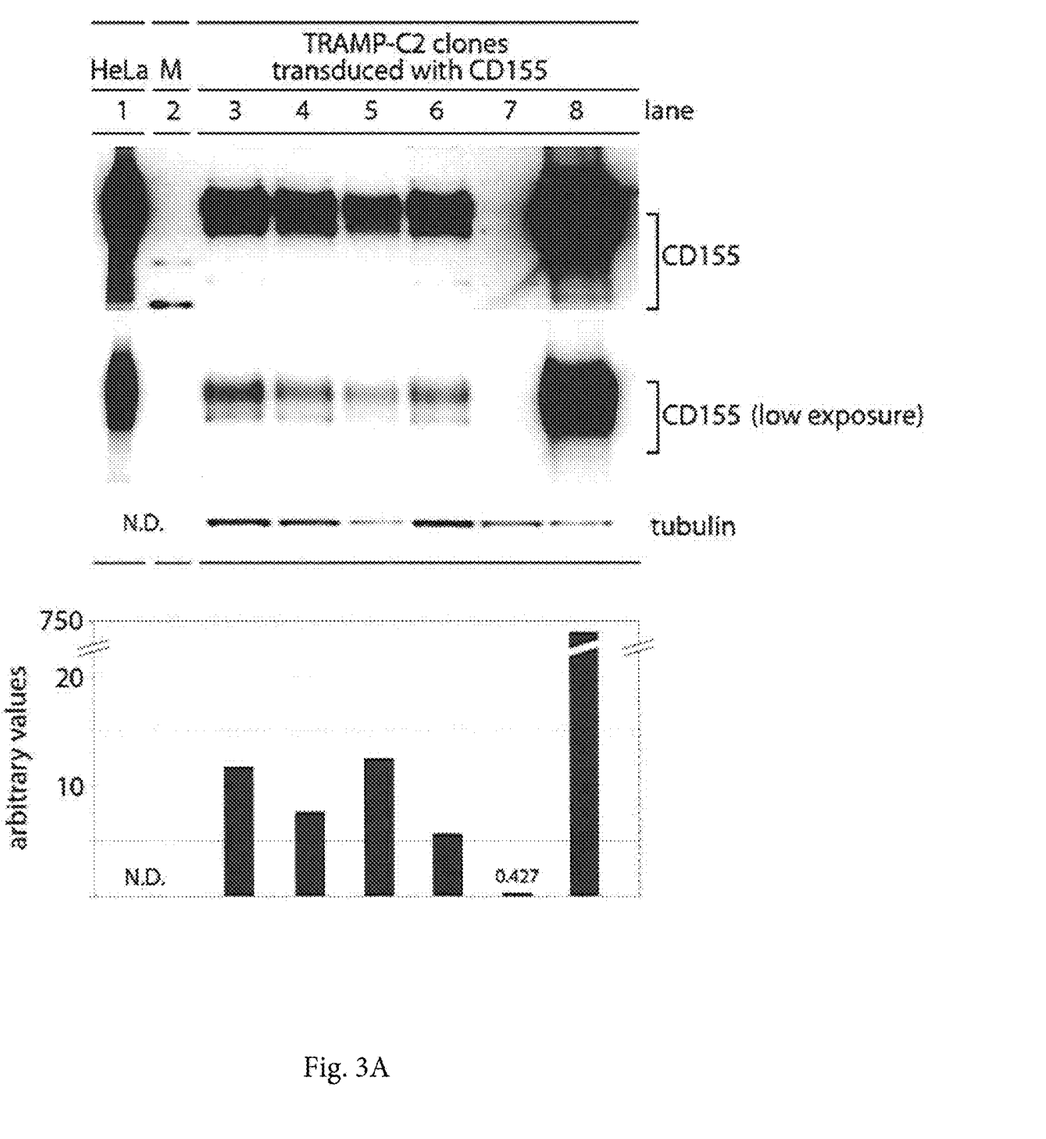
FIG. 3A shows CD155 immunoblot of lysates from a panel of transduced TRAMP-C2 lines; quantitation of immunoblot signal is shown below.
Figure 3B:
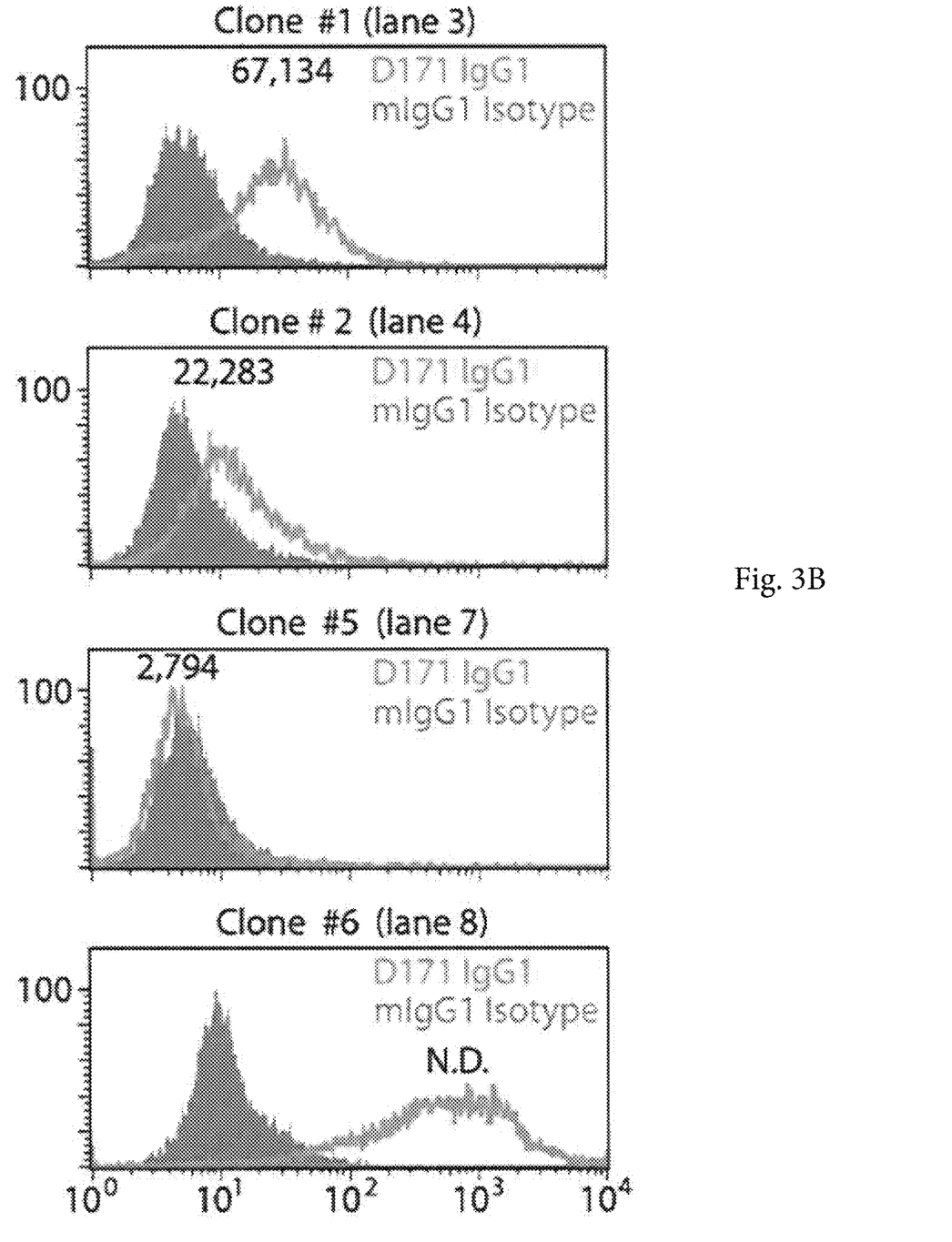
FIG. 3B shows standard FACS/qFACS analyses of CD155 in TRAMP-C2 clones 1, 2, 5, 6; lane numbers corresponding to FIG. 3A. Numbers atop the peaks represent CD155 receptors per cell as determined by qFACS (see Example 1); receptor numbers in clone 6 were outside the linear range and could not be evaluated (N.D.).

CD155 alone is sufficient for mediating PV susceptibility[6] and positive CD155 IHC correlates with known sites for PV replication (FIG. 1D, F, H). Thus, CD155 expression suggests virtually universal susceptibility of glioblastoma to PVSRIPO.[3] However, since CD155 expression in glioblastoma was variable: it is unknown if CD155 expression levels influence PVSRIPO tumor targeting. To test this, we carried out tests in a genetically engineered mouse prostate cancer model, TRAMP-C2,[29] transduced with human CD155. The mouse CD155 homolog does not function as a PV receptor and, thus, murine cells do not allow PV entry. Therefore, ectopic PV receptor expression in TRAMP-C2 cells enables tests to correlate CD155 expression levels with PV susceptibility. Six TRAMP-C2 clones, selected for stable transduction with CD155, exhibited inherently distinct CD155 expression levels (FIG. 3A). Immunoblot signal for the lowest-expressing clone #5 was exceedingly weak and was only apparent with excessive exposure (FIG. 3A). CD155 immunoblot signal in the highest-expressing clone #6 exceeded clone #5 ~1,700-fold (FIG. 3A). Diverging expression was also evident in FACS/qFACS analyses (FIG. 3B). We carried out PVSRIPO infections of TRAMP-C2 clones

Figure 3C:
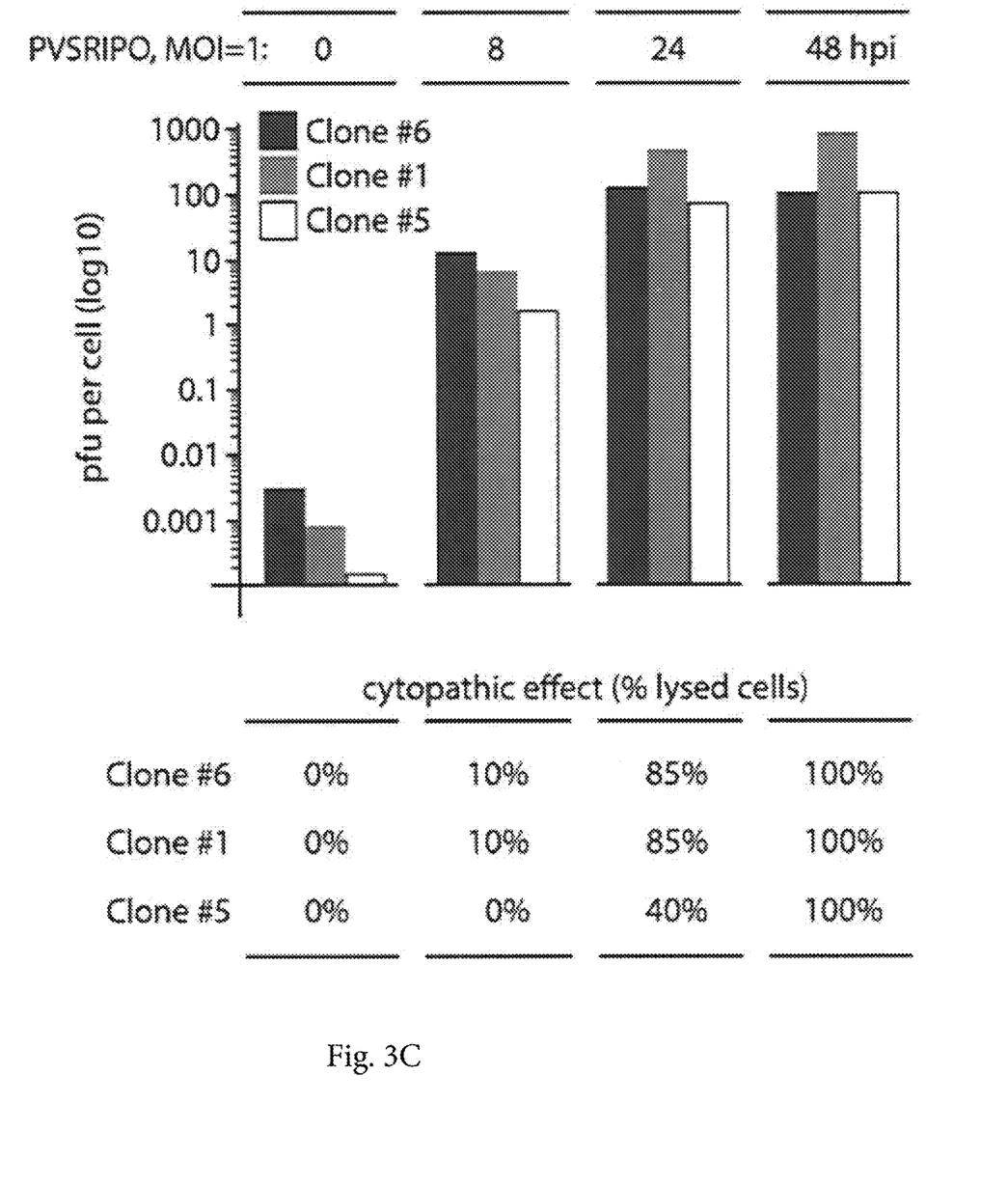
FIG. 3C shows results of infection of TRAMP-C2 clone 1, 5 and 6 cultures with PVSRIPO (MOI=1), which were lysed at the indicated intervals, and plaque forming units (pfu) per cell were determined by standard plaque assay. The bottom panel indicates the approximate percentage of cells exhibiting cytopathogenic effects (CPE) in infected cultures.

5 and #6, representing expression extremes, and in clone #1 with intermediate CD155 levels, and assessed viral propagation and cytopathogenicity (FIG. 3C). One-step growth curves of PVSRIPO revealed enhanced attachment in clone #6 vs. clone #5, evident as ~15-fold elevated recovery of infectious particles from cultures lysed after a 30 min 'attachment step' at room temperature[23] (FIG. 3C). This suggests that elevated CD155 expression levels favor virus attachment to cells, an expected finding. However, with the progress of virus propagation (upon transfer of infected cultures to 37° C.), viral titers detected in infected clone #5 cultures caught up and were roughly even with clone #6 at 48 hrs post infection (FIG. 3C). PV/PVSRIPO cause drastic, rapid cytopathogenic effects leading to gross morphological changes and cell detachment. Unsurprisingly, unbridled PVSRIPO propagation in clones #5 and #6 resulted in complete cytolysis 48 hrs post infection (FIG. 3C). These data suggest that even marginal CD155 immunoblot signal (FIG. 2F, 3A) corresponding to low IHC signal (FIG. 2A) is commensurate with full susceptibility to PVSRIPO infection and tumor cell killing and, hence, oncolytic immunotherapy.

EXAMPLE 6

For the immunohistochemistry (IHC) analysis we initially utilized the antibodies presented in the table 2 below. Examination of IHC results in FFPE sections by the study pathologist (REM) revealed a lack of reactivity/specificity of all tested antibodies, suggesting their unsuitability for a robust clinical assay.

TABLE 2

| Antibody | Source | IHC Specificity |
| --- | --- | --- |
| D171 | Mouse monoclonal antibody | No reactivity to tumor tissue |
| D480 | a rabbit polyclonal serum raised against the CD155 extracellular domain | Non-specific reactivity in tumor tissue |
| LifeSpanBio Cat No. LS-B10536 | A rabbit polyclonal CD155 antibody raised against KLH-conjugated synthetic peptide between amino acids 314-342 from C-terminal region of human PVR | Non-specific reactivity to PVR negative Raji cell line |
| Biolegend Cat No. 337602 | Affinity chromatography purified mouse IgG, κ | No reactivity to tumor tissue |

We then evaluated a newly developed rabbit anti-CD155 mAb [Cell Signaling (D3G7H)] and the novel features and advantages of utilizing this antibody for CD155 IHC analysis are listed below.
1) D3G7H is mono-specific for human CD155 in immunoblot in murine tissues;
2) D3G7H is devoid of immune-reactivity in a confirmed CD155-negative human-derived tissue;
3) D3G7H detects CD155 in normal primate/human tissues known to support PV infection/replication;
4) D3G7H recognizes CD155 in cells that may not support productive PV replication (e.g., vascular endothelium), but execute physiologic functions associated with CD155 expression.

REFERENCES

The disclosure of each reference cited is expressly incorporated herein.
1. Stupp R, Hegi M E, Mason W P, et al. Effects of radiotherapy with concomitant and adjuvant temozolomide versus radiotherapy alone on survival in glioblastoma in a randomised phase III study: 5-year analysis of the EORTC-NCIC trial. Lancet Oncol. 2009; 10(5):459-466.
2. Gromeier M, Lachmann S, Rosenfeld M R, Gutin P H, Wimmer E. Intergeneric poliovirus recombinants for the treatment of malignant glioma. Proc Natl Acad Sci U S A. 2000; 97(12):6803-6808.
3. Brown M C, Dobrikova E Y, Dobrikov M I, et al. Oncolytic polio virotherapy of cancer. Cancer. 2014; 120(21):3277-3286.
4. Takai Y, Miyoshi J, Ikeda W, Ogita H. Nectins and nectin-like molecules: roles in contact inhibition of cell movement and proliferation. Nat Rev Mol Cell Biol. 2008; 9(8):603-615.
5. Universal Protein Resource (uniprot) entry number P15151.
6. Mendelsohn C L, Wimmer E, Racaniello V R. Cellular receptor for poliovirus: molecular cloning, nucleotide sequence, and expression of a new member of the immunoglobulin superfamily. Cell. 1989; 56(5):855-865.
7. He Y, Mueller S, Chipman P R, et al. Complexes of poliovirus serotypes with their common cellular receptor, CD155. J Virol. 2003; 77(8):4827-4835.
8. Koike S, Horie H, Ise I, et al. The poliovirus receptor protein is produced both as membrane-bound and secreted forms. EMBO J. 1990; 9(10):3217-3224.
9. Wimmer E, Harber, J. J., Bibb, J. A., Gromeier, M., Lu, H. H., and Bernhardt, G. Poliovirus receptors. In ªCellular Receptors for Animal Virusesº (E. Wimmer, Ed.). Cold Spring Harbor Laboratory Press, Plainview, N.Y. 1993: pp. 101-128.
10. Belnap D M, McDermott B M, Jr., Filman D J, et al. Three-dimensional structure of poliovirus receptor bound to poliovirus. Proc Natl Acad Sci USA. 2000;97(1):73-78.
11. Bernhardt G, Harber J, Zibert A, deCrombrugghe M, Wimmer E. The poliovirus receptor: identification of domains and amino acid residues critical for virus binding. Virology. 1994;203(2):344-356.
12. He Y, Bowman V D, Mueller S, et al. Interaction of the poliovirus receptor with poliovirus. Proc Natl Acad Sci USA. 2000;97(1):79-84.
13. Bodian D. Emerging concept of poliomyelitis infection. Science. 1955;122(3159):105-108.
14. Sabin A B. Pathogenesis of poliomyelitis; reappraisal in the light of new data. Science. 1956;123(3209):1151-1157.
15. Iwasaki A, Welker R, Mueller S, Linehan M, Nomoto A, Wimmer E. Immunofluorescence analysis of poliovirus receptor expression in Peyer's patches of humans, primates, and CD155 transgenic mice: implications for poliovirus infection. J Infect Dis. 2002;186(5):585-592.
16. Blinzinger K, Simon J, Magrath D, Boulger L. Poliovirus crystals within the endoplasmic reticulum of endothelial and mononuclear cells in the monkey spinal cord. Science. 1969;163(3873):1336-1337.
17. Freistadt M S, Fleit H B, Wimmer E. Poliovirus receptor on human blood cells: a possible extraneural site of poliovirus replication. Virology. 1993;195(2):798-803.
18. Carlson B L, Pokorny J L, Schroeder M A, Sarkaria J N. Establishment, maintenance and in vitro and in vivo applications of primary human glioblastoma multiforme (GBM) xenograft models for translational biology studies and drug discovery. Curr Protoc Pharmacol. 2011; Chapter 14:Unit 14 16.
19. Nobis P, Zibirre R, Meyer G, Kuhne J, Warnecke G, Koch G. Production of a monoclonal antibody against an 20. Merrill M K, Bernhardt G, Sampson R I, Wikstrand C J, Bigner D D, Gromeier M. Poliovirus receptor CD155-targeted oncolysis of glioma. *Neuro Oncol.* 2004;6(3): 208-217.
21. Wolff A C, Hammond M E, Schwartz J N, et al. American Society of Clinical Oncology/College of American Pathologists guideline recommendations for human epidermal growth factor receptor 2 testing in breast cancer. *J Clin Oncol.* 2007;25(1):118-145.
22. Dobrikov M I, Dobrikova E Y, Gromeier M. Dynamic regulation of the translation initiation helicase complex by mitogenic signal transduction to eukaryotic translation initiation factor 4G. *Mol Cell Biol.* 2013;33(5):937-946.
23. Brown M C, Bryant J D, Dobrikova E Y, et al. Induction of viral, 7-methyl-guanosine cap-independent translation and oncolysis by mitogen-activated protein kinase-interacting kinase-mediated effects on the serine/arginine-rich protein kinase. *J Virol.* 2014;88(22):13135-13148.
24. Wikstrand C J, McLendon R E, Friedman A H, Bigner D D. Cell surface localization and density of the tumor-associated variant of the epidermal growth factor receptor, EGFRvIII. *Cancer Res.* 1997;57(18):4130-4140.
25. Freistadt M S, Kaplan G, Racaniello V R. Heterogeneous expression of poliovirus receptor-related proteins in human cells and tissues. *Mol Cell Biol.* 1990;10(11): 5700-5706.
26. Solecki D, Schwarz S, Wimmer E, Lipp M, Bernhardt G. The promoters for human and monkey poliovirus receptors. Requirements for basic and cell type-specific activity. *J Biol Chem.* 1997;272(9):5579-5586.
27. Boulger L R, Arya S C, Ahourai P, Marsden S A. International comparison of species of monkey used for the neurovirulence test for oral poliomyelitis vaccine. *J Biol Stand.* 1978;6(3):233-242.
28. Reymond N, Imbert A M, Devilard E, et al. DNAM-1 and PVR regulate monocyte migration through endothelial junctions. *J Exp Med.* 2004;199(10):1331-1341.
29. Greenberg N M, DeMayo F, Finegold M J, et al. Prostate cancer in a transgenic mouse. *Proc Natl Acad Sci USA.* 1995;92(8):3439-3443.
30. Geraghty R J, Krummenacher C, Cohen G H, Eisenberg R J, Spear P G. Entry of alphaherpesviruses mediated by poliovirus receptor-related protein 1 and poliovirus receptor. *Science.* 1998;280(5369):1618-1620.
31. Bottino C, Castriconi R, Pende D, et al. Identification of PVR (CD155) and Nectin-2 (CD112) as cell surface ligands for the human DNAM-1 (CD226) activating molecule. *J Exp Med* 2003;198(4):557-567.
32. Martinet L, Smyth M J. Balancing natural killer cell activation through paired receptors. Nat Rev Immunol. 2015;15(4):243-254.
33. Erickson B M, Thompson N L, Hixson D C. Tightly regulated induction of the adhesion molecule necl-5/CD155 during rat liver regeneration and acute liver injury. *Hepatology.* 2006;43(2):325-334.
34. Soriani A, Zingoni A, Cerboni C, et al. ATM-ATR-dependent up-regulation of DNAM-1 and NKG2D ligands on multiple myeloma cells by therapeutic agents results in enhanced NK-cell susceptibility and is associated with a senescent phenotype. *Blood.* 2009;113(15): 3503-3511.
35. Carlsten M, Norell H, Bryceson Y T, et al. Primary human tumor cells expressing CD155 impair tumor targeting by down-regulating DNAM-1 on NK cells. *J Immunol.* 2009;183(8):4921-4930.
36. Castriconi R, Daga A, Dondero A, et al. NK cells recognize and kill human glioblastoma cells with stem cell-like properties. *J Immunol.* 2009;182(6):3530-3539.
37. Matusali G, Potesta M, Santoni A, Cerboni C, Doria M. The human immunodeficiency virus type 1 Nef and Vpu proteins downregulate the natural killer cell-activating ligand PVR. *J Virol.* 2012;86(8):4496-4504.
38. Tomasec P, Wang E C, Davison A J, et al. Downregulation of natural killer cell-activating ligand CD155 by human cytomegalovirus UL141. *Nat Immunol.* 2005;6(2): 181-188.
39. Casado J G, Pawelec G, Morgado S, et al. Expression of adhesion molecules and ligands for activating and costimulatory receptors involved in cell-mediated cytotoxicity in a large panel of human melanoma cell lines. *Cancer Immunol Immunother.* 2009;58(9):1517-1526.

We claim:

1. A method of treating a CD155-expressing cancer in a subject, comprising:
   (a) obtaining a tumor tissue sample from the subject;
   (b) contacting the tumor tissue sample under conditions suitable for antibody-antigen binding with a primary antibody D3G7H, which specifically binds to an epitope on CD155 comprising residue R172 of SEQ ID NO:1 (CD155);
   (c) detecting the primary antibody that is bound to the tumor tissue sample; and
   (d) administering a PVSRIPO oncolytic immunotherapy to the subject to treat a CD155-expressing cancer expressing the epitope on CD155 comprising residue R172 of SEQ ID NO:1 (CD155).

2. The method of claim 1, wherein the primary antibody is monoclonal.

3. The method of claim 1, wherein the primary antibody is a rabbit antibody.

4. The method of claim 1, wherein the tumor tissue sample is fixed.

5. The method of claim 1, wherein the tumor tissue sample is frozen.

6. The method of claim 1, wherein the tumor tissue sample is from a formalin fixed, paraffin embedded sample.

7. The method of claim 1, wherein the tumor tissue sample is a brain tumor tissue.

8. The method of claim 1, wherein the tumor tissue sample is a glioblastoma tumor tissue.

9. The method of claim 1, wherein the tumor tissue sample is selected from the group consisting of: medulloblastoma, atypical teratoid rhabdoid tumor (ATRT), primitive neuroectodermal tumor (PNET), meningioma, anaplastic ependymoma, pleomorphic xanthoastrocytoma (PXA), and prostate.

10. The method of claim 1, wherein step (b) further comprises the step of contacting the tumor tissue sample with a secondary antibody under conditions suitable for antibody-antigen binding, wherein the secondary antibody binds to the primary antibody.

11. The method of claim 10, further comprising the step of detecting the secondary antibody.

12. The method of claim 10, wherein the secondary antibody is labeled.

13. The method of claim 12, wherein the secondary antibody is radiolabeled or fluorescently labeled.

14. The method of claim 10, wherein the secondary antibody is conjugated to horseradish peroxidase.

15. The method of claim 10, wherein the secondary antibody is an anti-rabbit antibody.

16. The method of claim 1, wherein the epitope is in residues 165-182 of SEQ ID NO:1 (CD155).

17. The method of claim 1, wherein the epitope is selected from the group consisting of SEQ ID NO:2, SEQ ID NO:3, SEQ ID NO:4, SEQ ID NO:5 and SEQ ID NO:6.

* * * * *